(12) United States Patent
Higuchi et al.

(10) Patent No.: US 7,316,984 B2
(45) Date of Patent: Jan. 8, 2008

(54) TEXTILE PRODUCT

(75) Inventors: Ryouichi Higuchi, Kawasaki (JP); Nobuyoshi Kitamura, Kawasaki (JP); Sadakazu Hirose, Ayabe (JP); Hideo Sukeda, Ayabe (JP); Shiro Suzuki, Ayabe (JP); Katsuya Anno, Osaka (JP)

(73) Assignee: Ajinomoto Co., Inc., Tokyo (JP)

( * ) Notice: Subject to any disclaimer, the term of this patent is extended or adjusted under 35 U.S.C. 154(b) by 616 days.

(21) Appl. No.: 10/258,733

(22) PCT Filed: Apr. 27, 2001

(86) PCT No.: PCT/JP01/03687

§ 371 (c)(1), (2), (4) Date: Apr. 2, 2003

(87) PCT Pub. No.: WO01/83875

PCT Pub. Date: Nov. 8, 2001

(65) Prior Publication Data

US 2003/0157310 A1    Aug. 21, 2003

(30) Foreign Application Priority Data

Apr. 28, 2000   (JP)   ............................. 2000-130006

(51) Int. Cl.
*B32B 21/02* (2006.01)
*B32B 21/10* (2006.01)
*D06M 10/00* (2006.01)
*D06M 13/322* (2006.01)
*D21J 1/00* (2006.01)

(52) U.S. Cl. ................... 442/59; 428/292.4; 8/196; 8/127.6; 8/115.66

(58) Field of Classification Search .................. 442/59
See application file for complete search history.

(56) References Cited

U.S. PATENT DOCUMENTS

| | | | | |
|---|---|---|---|---|
| 4,069,214 A | | 1/1978 | Onizawa | ...................... 260/78 |
| 4,150,945 A | * | 4/1979 | Onizawa | ...................... 8/115.6 |
| 4,438,095 A | * | 3/1984 | Grollier et al. | .......... 424/70.13 |
| 5,100,655 A | * | 3/1992 | Takano et al. | ................. 424/63 |
| 5,306,444 A | | 4/1994 | Kitamura et al. | ........... 252/546 |
| 5,366,665 A | * | 11/1994 | Cho | ........................... 510/152 |
| 5,482,764 A | | 1/1996 | McBride et al. | .............. 428/96 |
| 5,728,461 A | * | 3/1998 | Nogata et al. | ............... 428/372 |
| 6,221,382 B1 | * | 4/2001 | Ishida et al. | ................ 424/443 |
| 2002/0013249 A1 | * | 1/2002 | Nakagawa | .................. 510/384 |

FOREIGN PATENT DOCUMENTS

| | | |
|---|---|---|
| EP | 1 118 705 A2 | 7/2001 |
| EP | 1 118 705 A3 | 10/2001 |
| JP | 05-36534 | 5/1993 |
| JP | 08-60547 | 3/1996 |
| JP | 09-157152 | 6/1997 |
| JP | 11-093075 | 4/1999 |
| JP | 2000-045173 | 2/2000 |
| JP | 2000-199178 | 7/2000 |
| JP | 2000-238423 | 9/2000 |
| JP | 2000-265380 | 9/2000 |

OTHER PUBLICATIONS

International Search Report dated Jul. 13, 2001.
Chinese Intellectual Property Office communication for corresponding Chinese Patent Application No. 028141458 dated Dec. 24, 2004, English version.
Chinese Intellectual Property Office communication for corresponding Chinese Patent Application No. 01808745.0 dated Dec. 24, 2004, English version and Chinese version.

* cited by examiner

*Primary Examiner*—Elizabeth M. Cole
*Assistant Examiner*—Matthew D. Matzek
(74) *Attorney, Agent, or Firm*—Edwards Angell Palmer & Dodge LLP

(57) ABSTRACT

A textile product having arginine imparted thereto; a process for producing the product; and a method for the pretreatment of a textile product. The textile product compensates for the water-retaining function of the horny layer and enhances metabolism. It hence has the effect of keeping the skin normal.

13 Claims, 3 Drawing Sheets

TEXTILE PRODUCT

TECHNICAL FIELD

The present invention relates to a textile product which is used to preserve skin moisture and a processing method for such a product, and in particular to a textile product having the effect of preserving normal skin by supplementing the moisture retention function of the stratum corneum and by enhancing metabolism.

BACKGROUND ART

Pyrrolidonecarboxylic acid (PCA) or amino acids such as arginine are natural moisturizing factors inherently found in the human body, and have been scrutinized for their skin care properties. Although the use of protein fibers and the provision of proteins to textile products are known (Japanese Unexamined Patent Publication H8-60547 and Japanese Examined Patent Publication H5-36534), there have not been any textile products which have been endowed with skin care properties by processing a textile product using an amino acid such as arginine.

An object of the present invention is to provide a textile product which has the effect of preserving normal skin by supplementing the moisture retention function of the stratum corneum and by enhancing metabolism, while retaining the inherent properties of fiber materials, and in particular is to give a novel function to textile products which are close-fitting on the skin, such as underwear, stockings, socks, and gloves made of synthetic fibers which have poor moisture absorption, such as nylon and polyester.

DISCLOSURE OF THE INVENTION

Figure 1:
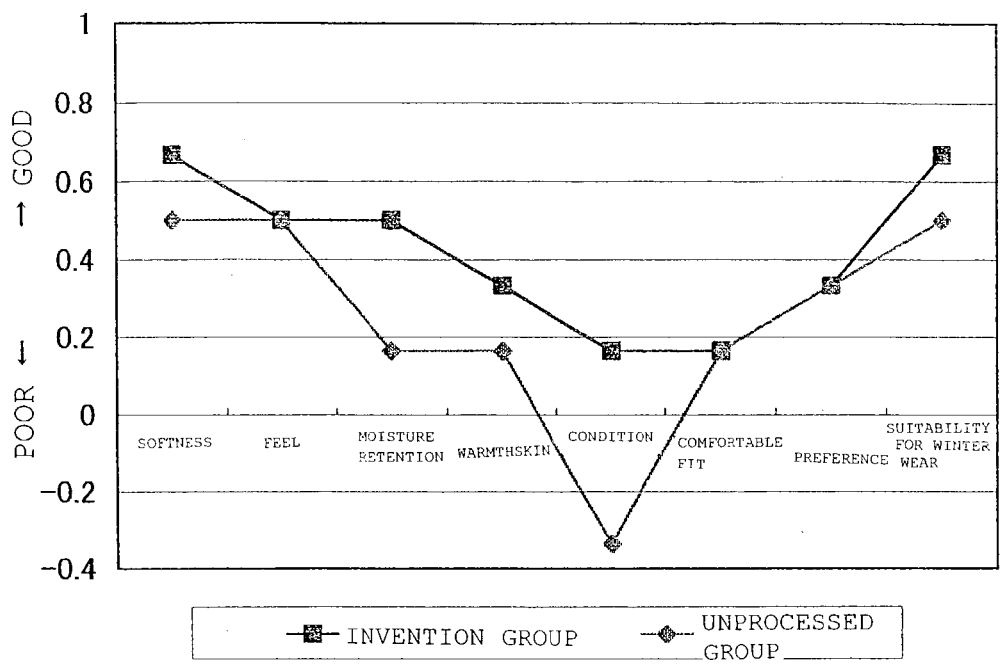
FIG. 1 shows the results of evaluation after wearing the tights of the present invention for a long period of time.
Figure 2:
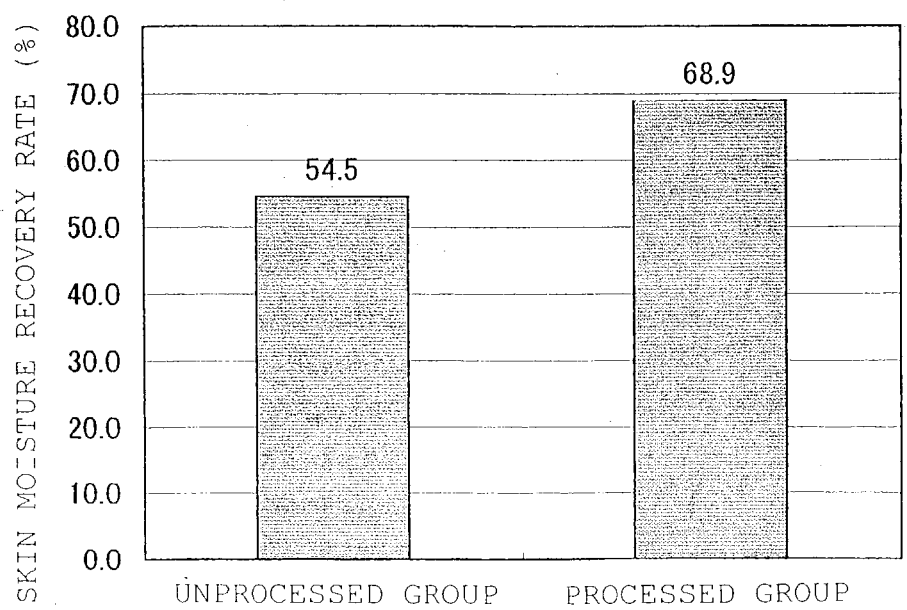
FIG. 2 shows the results from test example 2.

The invention relates to the following matters 1 through 12.

1. A textile product to which arginine is provided.
2. The textile product according to 1, to which arginine is provided along with a binder.
3. The textile product according to 1, to which pyrrolidonecarboxylic acid is further provided.
4. The textile product according to 2, to which pyrrolidonecarboxylic acid is further provided;
5. The textile product according to 1, to which arginine is provided in an amount of about 0.05 to 10 wt % relative to the fiber weight.
6. The textile product according to 3, to which arginine is provided in an amount of about 0.05 to 10 wt % relative to the fiber weight, and to which pyrrolidonecarboxylic acid is provided in an amount of about 0.05 to 5 wt % relative to the fiber weight.
7. The textile product according to 2, wherein the binder comprises a cationic acrylic binder;
8. The textile product according to 2, wherein the binder comprises a cationic acrylic binder and a silica dispersant.
9. A method for processing a textile product, characterized in that a textile product is pre-treated with a fiber pre-treatment agent comprising a binder, and is then treated with a treatment solution comprising arginine and optionally, pyrrolidonecarboxylic acid.
10. The processing method according to 9, wherein the binder contained in the fiber pre-treatment agent comprises a cationic acrylic binder.
11. The processing method according to 9, wherein the binder contained in the fiber pre-treatment agent comprises a cationic acrylic binder and a silica dispersant.
12. A method for pre-treating a textile product, wherein a textile product is pre-treated with a cationic acrylic binder and a silica dispersant.

Examples of fiber materials include natural fibers such as cotton, flax, silk, and wool, and synthetic fibers such as nylon, rayon, polyester, cupra, acetate, and acrylic.

Examples of textile products include fibrils, yarn, pile, flocked material, weaves, knits, non-woven fabric, and cotton-like materials, and more specifically clothing such as underwear, athletic supports, socks, stockings, tights, and gloves.

The textile products in the present invention are preferably pre-treated with a fiber pre-treatment agent to enhance the washability of the arginine. Textile products comprising arginine and a binder are preferred, and textile products comprising arginine, a binder, and a silica dispersant are even more desirable.

Examples of fiber pre-treatment agents include acrylic-, urethane-, polyester-, or epoxy-based binders, silica dispersants, and the like. The binder is preferably a cationic binder (positively charged).

The textile product pre-treatment and the arginine and pyrrolidonecarboxylic acid treatment can involve the use of means such as dipping, coating, or spraying, but the textile is preferably treated by being dipped.

The textile product in the present invention should be pre-treated with a cationic acrylic binder and a silica dispersant, and should then be treated with arginine and, if needed, pyrrolidonecarboxylic acid. The pre-treatment can be managed, for example, by dipping a textile product for 5 to 30 minutes in a 40 to 80° C. solution comprising a cationic acrylic binder and a silica dispersant, and then centrifugally drying the textile. The concentration of the cationic acrylic binder in the pre-treatment solution is between about 0.5 and 5 wt %, and the concentration of the silica dispersant is between about 0.5 and 5 wt %.

An example of a cationic acrylic binder is LIGHT-EPOCH BX-71 (tradename, by Kyoeisha Chemical Co., Ltd.).

An example of a silica dispersant is CLA-110 (tradename, by Kyoeisha Chemical Co., Ltd.).

When pre-treatment is undertaken with a fiber pre-treatment agent, the pre-treatment agent is left over in an amount of about 0.05 to 10 wt %, and preferably about 0.3 to 5 wt % of the fiber.

When the pre-treatment is undertaken with a fiber pre-treatment agent comprising a cationic acrylic binder, the amount of cationic acrylic binder in the fiber after the pre-treatment is about 0.05 to 5 wt %, and preferably about 0.3 to 2 wt %.

When the pre-treatment is undertaken with a fiber pre-treatment agent comprising a cationic acrylic binder and a silica dispersant, the amount of cationic acrylic binder in the fiber after the pre-treatment is about 0.05 to 5 wt %, and preferably about 0.3 to 2 wt %, and the amount of silica dispersant is 0.01 to 5 wt %, and preferably 0.02 to 0.5 wt %.

Such pre-treatment can improve the washability when chemicals are subsequently applied.

The arginine can be provided preferably by dipping the pre-treated fiber product for 5 to 30 minutes in a 40 to 60° C. treatment solution comprising 5 to 20 (g/L) of arginine, and then centrifugally drying the textile. When pyrrolidonecarboxylic acid is provided along with the arginine, the textile is similarly treated using a treatment solution comprising 5 to 20 (g/L) of arginine and 5 to 20 (g/L) of pyrrolidonecarboxylic acid. The pH of the treatment solution is preferably adjusted to between about 6.0 and 7.0 in order to prevent loss of dye. The treatment agent comprising the arginine may also include 2 to 5 wt % of softener (such as WS-937, by Marue Yuka KK).

The arginine may be free arginine, a salt with an inorganic acid such as hydrochloric acid, sulfuric acid, nitric acid, or phosphoric acid, an organic acid salt such as a citrate, succinate, p-toluenesulfonate, or methanesulfonate, or a salt with a base such as sodium or potassium.

The pyrrolidonecarboxylic acid may be in the form of a free pyrrolidonecarboxylic acid, or a salt with a base such as sodium or potassium.

The arginine is provided in an amount of about 0.05 to 10 wt %, and preferably about 2 to 10 wt %, relative to the fiber weight.

When pyrrolidonecarboxylic acid is provided along with the arginine, the arginine is provided in an amount of about 0.05 to 10 wt %, and preferably about 2 to 10 wt %, relative to the fiber weight, and the pyrrolidonecarboxylic acid is provided in an amount of about 0.05 to 5 wt %, and preferably about 0.5 to 5 wt %, relative to the fiber weight.

The arginine retention of the textile product in the present invention after 10 washings should be at least 60%, preferably at least 75%, and even more preferably at least 90%. The arginine retention after 20 washings should be at least 50%, preferably at least 65%, and even more preferably at least 80%.

The textile product of the present invention has better skin care properties such as better skin moisture content.

The textile product of the present invention pre-treated with the fiber pre-treatment agent has good washability and longer-lasting skin care properties.

BEST MODE FOR CARRYING OUT THE INVENTION

The present invention is illustrated in further detail in the following examples.

EXAMPLE 1

(1) Skin Care Processing 37.792 g nylon tights fabric was dipped in a 40° C. treatment solution (380 mL) containing a cationic acrylic binder (2% owf, tradename: LIGHT-EPOCH BX-71 (by Kyoeisha Chemical Co., Ltd.)), silica dispersant (2% owf, tradename: CLA-110 (by Kyoeisha Chemical Co., Ltd.)), and softener (2% owf, tradename: WS-937, by Marue Yuka KK), and was then centrifugally dried for 15 seconds, giving fabric with a 50 to 60% moisture content. The resulting fabric was dipped for 30 minutes in 40° C. treatment solution (pH 6.0) containing arginine (Arg: 10 g/L) and sodium pyrrolidonecarboxylate (PCA-Na: 15 g/L), and was then centrifugally dried for 15 seconds, giving a skin care processed tights fabric with a 50 to 60% moisture content, which was dried to give tights fabric for the test below.

EXAMPLE 2

37.692 g nylon tights fabric was dipped, without being pre-treated, for 30 minutes in 40° C. treatment solution (pH 6.0) containing arginine (Arg: 10 g/L) and sodium pyrrolidonecarboxylate (15 g/L) under the same conditions as in Example 1, and was then centrifugally dried for 15 seconds, giving a skin care processed tights fabric with a 50 to 60% moisture content, which was dried to give tights fabric for the following test.

TEST EXAMPLE 1

Laundering Test

According to JIS 0217 103 method, 5.0 g of the fabrics obtained in Examples 1 and 2 were washed for 5 minutes in 150 mL of 40° C. tepid water at a bath ratio of 1:30 using 0.67 g/L (standard amount) of the detergent Attack (tradename, by Kao Corp.), and the fabrics wee then rinsed. The total amount of washing solution was 1460 mL. The fabrics were washed 20 times, and the amounts of arginine and pyrrolidonecarboxylic acid that were lost were measured by liquid chromatography to determine the retention.

The adhering amounts which are given in Table 2 were determined in the following manner.

<Method for Measurement of Adhering Amount>

The amounts that adhered were determined by subtracting the amounts of arginine and sodium pyrrolidonecarboxylate present in the treatment solution left over after the dipping and the treatment solution which was wrung from the textile from the amounts of arginine and sodium pyrrolidonecarboxylate present in the treatment solution before the tights fabrics were dipped. The amounts of arginine and sodium pyrrolidonecarboxylate were determined by measurement using liquid chromatography.

The results are given in Table 1.

TABLE 1

|  | Example 1 | Example 2 |
|---|---|---|
| Pre-treatment | yes | no |
| Pre-processing weight (g) | 37.792 | 37.692 |
| Amount adhering (g) (adhesion rate %) |  |  |
| Arg | 1.316 (3.48) | 0.442 (1.17) |
| PCA-Na | 0.363 (0.96) | 0.092 (0.24) |
| Retention (%) after 10 washings |  |  |
| Arg | 90.729 | 67.421 |
| PCA-Na | 72.452 | 0 |
| Retention (%) after 20 washings |  |  |
| Arg | 84.1 | — |
| PCA-Na | 60.3 | — |

TEST EXAMPLE 2

Skin Moisture Measuring Test

Three subjects washed their lower arms (3 cm×3 cm) with 2 mL of sodium laurate 10% solution and dried them for 5 minutes, a washing step that was repeated 3 times to produce a model of dry skin, the fabric obtained in Examples 1 and 2 and unprocessed fabric were then applied, and the skin moisture content was measured with a SKICON-200 (tradename: by IBS) after 30 minutes and 1 hour. The measuring conditions involved a temperature of 20° C. and 40% RH.

When the fabric of the present invention was applied, the skin moisture recovery rate was clearly better than when not applied. The results are given in Table 2.

The skin moisture recovery rate was measured in the following manner.

Measurement of Skin Moisture Recovery Rate

The skin moisture content X after the preparation of the model dry skin was first measured. The skin moisture content Y 30 minutes after the fabric obtained in Example 1 and unprocessed fabric had been applied was then measured, and the skin moisture recovery rate was determined using the following equation.

Skin moisture recovery rate (%)=(($Y$–$X$)/$X$)×100

TEST EXAMPLE 3

Long-Term Wearing Test

For two weeks, ten subjects wore tights made of the fabric obtained in Example 1 and unprocessed tights on alternating days for at least 8 hours a day to test 8 parameters consisting of softness, feel, moisture retention, warmth, skin condition, comfortable fit, preference, and suitability for winter wear. The skin moisture content of the heel after 2 weeks was determined using a SKICON-200 (tradename, by IBS). The measuring conditions involved a temperature of 20° C. and 40% RH. The results are given in Table 2 and FIG. 1. The tights were washed the day after being used and were worn again on the following day throughout the test period. The mean of the measured skin moisture content (µs) was obtained for the 10 subjects.

TABLE 2

| Tights | Measured skin moisture content (µs) |
| --- | --- |
| Example 1 | 39.17 |
| Unprocessed product | 32.56 |

TEST EXAMPLE 4

Long-Term Wearing Test with Dry Skin

Three subjects with dry skin from among the 10 subjects in Test Example 3 wore tights made of the fabric obtained in Example 1 (right leg: processed group) and unprocessed tights (left leg: unprocessed group) for 7 days each, at least 8 hours a day. The skin moisture content of the lower legs and heels was measured after 7 days using a SKICON-200. The results were given in Table 3. The skin moisture content (µs) given in Table 3 is the mean for the 3 subjects.

TABLE 3

| | Skin moisture content (µs) |
| --- | --- |
| Right lower leg | 2.33 |
| Right heel | 69.00 |
| Left lower leg | 0.11 |
| Left heel | 34.44 |

Figure 3:
FIG. 3 is a photograph of a replica of a shin before wearing the tights of the invention.
Figure 4:
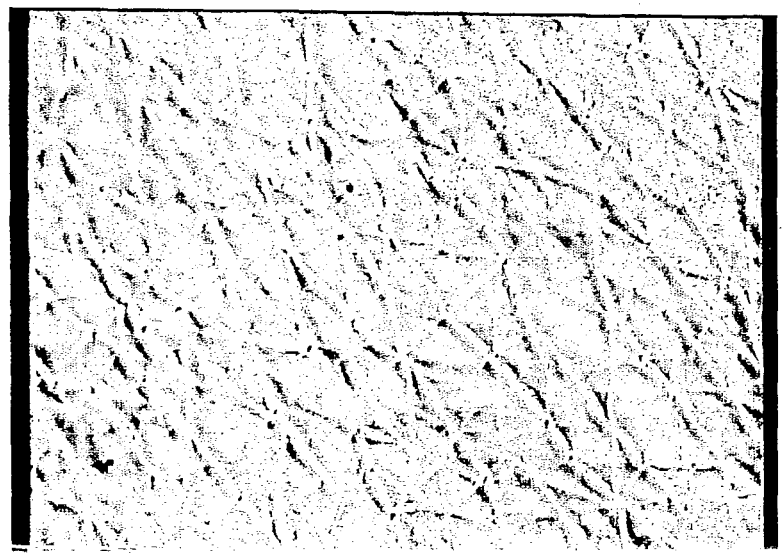
FIG. 4 is a photograph of a replica of a shin after wearing the tights of the invention for 14 days.

FIGS. 3 and 4 are photographs of a replica of a shin before and after the tights were worn.

Figure 5:
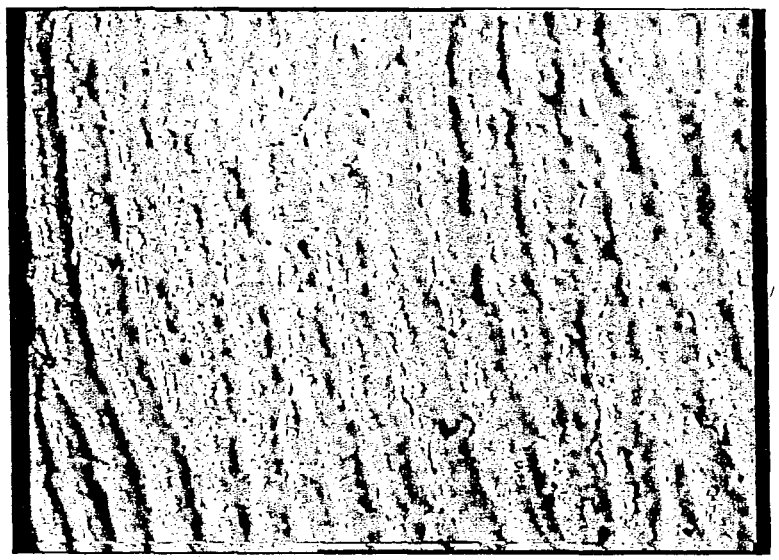
FIG. 5 is a photograph of a replica of a heel before wearing the tights of the invention.
Figure 6:
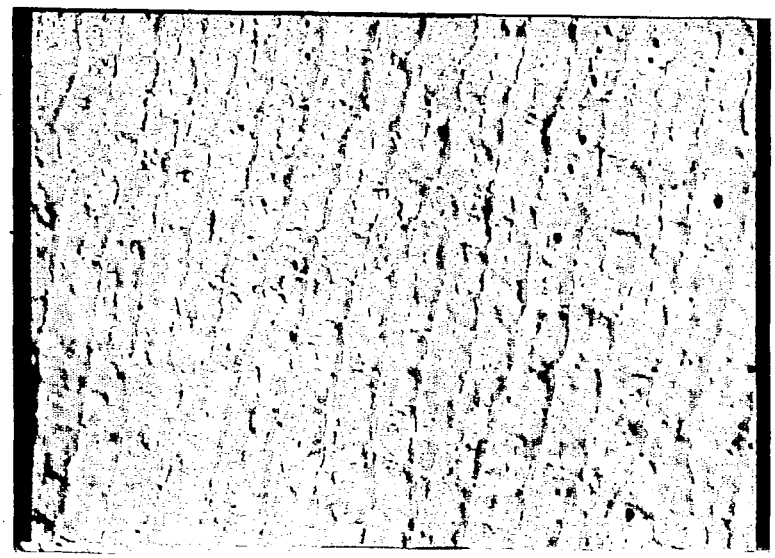
FIG. 6 is a photograph of a replica of a heel after wearing the tights of the invention for 14 days.

FIGS. 5 and 6 are photographs of a replica of a heel before and after the tights were worn.

The invention claimed is:

1. A textile product comprising arginine and a cationic binder, wherein arginine is free arginine or a salt of arginine with at least one member selected from the group consisting of hydrochloric acid, sulfuric acid, nitric acid, phosphoric acid, citric acid, succinic acid, p-toluenesulfonic acid, methanesulfonic acid, sodium and potassium.

2. The textile product according to claim 1 further comprising pyrrolidonecarboxylic acid.

3. The textile product according to claim 1 comprising arginine in an amount of about 0.05 to 10 wt % relative to the fiber weight.

4. The textile product according to claim 2 comprising arginine in an amount of about 0.05 to 10 wt % relative to the fiber weight and pyrrolidonecarboxylic acid in an amount of about 0.05 to 5 wt % relative to the fiber weight.

5. The textile product according to claim 1, wherein the cationic binder is a cationic acrylic binder.

6. The textile product according to claim 1 further comprising a silica dispersant.

7. The textile product according to claim 2 further comprising a silica dispersant.

8. A textile product consisting essentially of fibers treated with a cationic binder to which arginine is later added, wherein arginine is free arginine or a salt of arginine with at least one member selected from the group consisting of hydrochloric acid, sulfuric acid, nitric acid, phosphoric acid, citric acid, succinic acid, p-toluenesulfonic acid, methanesulfonic acid, sodium and potassium.

9. The textile product according to claim 8, to which pyrrolidonecarboxylic acid is further provided.

10. The textile product according to claim 8, to which arginine is provided in an amount of about 0.05 to 10 wt % relative to the fiber weight.

11. The textile product according to claim 8, to which arginine is provided in an amount of about 0.05 to 10 wt % relative to the fiber weight, and to which pyrrolidonecarboxylic acid is provided in an amount of about 0.05 to 5 wt % relative to the fiber weight.

12. The textile product according to claim 8, wherein the binder comprises a cationic acrylic binder.

13. The textile product according to claim 8, wherein the binder comprises a cationic acrylic binder and a silica dispersant.

* * * * *